United States Patent
Humphrey

(10) Patent No.: US 7,745,408 B2
(45) Date of Patent: Jun. 29, 2010

(54) METHOD OF INDUCING MELANOGENESIS IN HUMANS WITH MC1R VARIANT ALLELES

(75) Inventor: Stuart Michael Humphrey, Hampton (AU)

(73) Assignee: Clinuvel Pharmaceuticals Limited, Melbourne (AU)

( * ) Notice: Subject to any disclaimer, the term of this patent is extended or adjusted under 35 U.S.C. 154(b) by 379 days.

(21) Appl. No.: 10/595,971

(22) PCT Filed: Nov. 23, 2004

(86) PCT No.: PCT/AU2004/001630

§ 371 (c)(1),
(2), (4) Date: Jul. 2, 2007

(87) PCT Pub. No.: WO2005/048967

PCT Pub. Date: Jun. 2, 2005

(65) Prior Publication Data

US 2008/0004213 A1     Jan. 3, 2008

(30) Foreign Application Priority Data

Nov. 24, 2003 (AU) .............................. 2003906813

(51) Int. Cl.
*A61K 38/10* (2006.01)
*C07H 21/04* (2006.01)

(52) U.S. Cl. ...................................... 514/14; 536/24.33

(58) Field of Classification Search ........................ None
See application file for complete search history.

(56) References Cited

U.S. PATENT DOCUMENTS

| | | | |
|---|---|---|---|
| 4,457,864 | A | 7/1984 | Hruby et al. |
| 4,485,039 | A | 11/1984 | Hruby et al. |
| 4,866,038 | A | 9/1989 | Hruby et al. |
| 4,918,055 | A | 4/1990 | Hruby et al. |
| 5,049,547 | A | 9/1991 | Hruby et al. |
| 5,674,839 | A | 10/1997 | Hruby et al. |
| 5,683,981 | A | 11/1997 | Hadley et al. |
| 5,714,576 | A | 2/1998 | Hruby et al. |

FOREIGN PATENT DOCUMENTS

| | | |
|---|---|---|
| AU | 597630 | 6/1990 |
| AU | 618733 | 1/1992 |
| WO | 8704623 | 8/1987 |
| WO | 03072072 | 9/2003 |
| WO | 2005048967 | 6/2005 |

OTHER PUBLICATIONS

Epitan 2001 Annual Report 36 pages, accessed from http://www.clinuvel.com.au/resources/pdf/annual_reports/Annual_Report_2001.pdf.*

Abdel-Malek et al. (Feb. 1995) "Mitogenic and Melanogenic Stimulation of Normal Human Melanocytes by Melanotropic Peptides," Proc. Natl. Acad. Sci. USA 92(5):1789-1793.

Abdel-Malek et al. (Oct. 1999) "The Melanocortin-1 Receptor and Human Pigmentation," Ann. N.Y. Acad. Sci. 885:117-133.

Abel-Malek et al. (2000) "The Melanocortin-1 Receptor is a Key Regulator of Human Cutaneous Pigmentation," Pigment Cell Res. 13(Sup. 8):156-162.

Bastiaens et al. (2001) "Melanocortin-1 Receptor Gene Variants Determine the Risk of Nonmelanoma Skin Cancer Independently of Fair Skin and Red Hair," Am. J. Hum. Genet. 68(4):884-894.

Box et al. (1997) "Characterization of Melanocyte Stimulating Hormone Receptor Variant Alleles in Twins with Red Hair," Hum. Mol. Genet. 6(11):1891-1897.

De Luca et al. (1993) "Alpha Melanocyte Stimulating Hormone (Alpha MSH) Stimulates Normal Human Melanocyte Growth by Binding to High-Affinity Receptors," J. Cell. Sci. 105(4):1079-1084.

Dorr et al. (2000) "Increased Eumelanin Expression and Tanning is Induced by a Superpotent Melanotropin [Nle4-D-Phe7]-Alpha-MSH in Humans," Photochem. Photobiol. 72(4):526-532.

Dwyer et al. (1998) "The Use of Spectrophotometry to Estimate Melanin Density in Caucasions," Cancer Epidermiol. Biomarkers Prev. 7(3):203-206.

Dwyer et al. (2002) "Cutaneous Melanin Density of Caucasians Measured by Spectrophotometry and Risk of Malignant Melanoma Basal Cell Carcinoma, and Squamous Cell Carcinoma of the Skin," Am. J. Epidemiol. 155(7):614-621.

Fitzpatrick, T.B. (1988) "The Validity and Practicality of Sun-Reactive Skin Types I Through VI," Arch. Dermatol. 124(6):869-871.

Frandberg et al. (1998) "Human Pigmentation Phenotype: A Point Mutation Generates Nonfunctional MSH Receptor," Biochem. Biophys. Res. Commun. 245(2):490-492.

Healy et al. (2001) "Functional Variation of MC1R Alleles from Red-Haired Individuals," Hum. Mol. Genet. 10(21):2397-2402.

Hunt et al. (1994) "Alpha-Melanocyte Stimulating Hormone and Its Analogue Nle4DPhe7 Alpha-MSH Affect Morphology, Tyrosinase Activity and Melanogenesis in Cultured Human Melanocytes," J. Cell. Sci. 107(1):205-211.

Hunt et al. (1995) "Nle4DPhe7 Alpha-Melanocyte-Stimulating Hormone Increases the Eumelanin:Phaeomelanin Ratio in Cultured Human Melanocytes," J. Invest. Dermatol. 104(1):83-85.

(Continued)

*Primary Examiner*—Anish Gupta
*Assistant Examiner*—Ronald T Niebauer
(74) *Attorney, Agent, or Firm*—Greenlee, Winner and Sullivan, P.C.

(57) ABSTRACT

A method for inducing melanogenesis in a human subject having a melanocortin 1 receptor (MC1R) variant allele associated with loss of or diminished receptor function comprises administering to said subject an amount of an α-melanocyte stimulating hormone (α-MSH) analogue effective to induce melanogenesis by the melanocytes in the skin or other epidermal tissue of the subject.

9 Claims, 1 Drawing Sheet

OTHER PUBLICATIONS

Jimenez-Cervantes et al. (2001) "Thr40 and Met122 are New Partial Loss-of-Function Natural Mutations of the Human Melanocortin 1 Receptor," FEBS Lett. 508(1):44-48.

John et al. (2002) "Four Novel Variants in MC1R in Red-Haired South African Individuals of European Descent: S83P, Y152X, A171D, P256S," Hum. Mutat. 19(4):461-462.

Kadekaro et al. (Jun. 2003) "Significance of the Malenocortin 1 Receptor in Regulating Human Melanocyte Pigmentation, Proliferation, and Survival," Ann. N.Y. Acad. Sci. 994:359-365.

Kennedy et al. (2001) "Melanocortin 1 Receptor (MC1R) Gene Variants are Associated with and Increased Risk for Cutaneous Melanoma Which is Largely Independent of Skin Type and Hair Color," J. Invest Dermatol. 117(2):294-300.

Levine et al. (1991) "Induction of Skin Tanning by Subcutaneous Administration of a Potent Synthetic Melanotropin," JAMA 266(19):2730-2736.

Menon et al. (1983) "A Comparative Study of the Physical and Chemical Properties of Melanins Isolated from Human Black and Red Hair," J. Invest. Dermatol. 80(3):202-206.

Menon et al. (1983) "Effects of Ultraviolet-Visible Irradiation in the Presence of Melanin Isolated from Human Black or Red Hair Upon Ehrlich Ascites Carcinoma Cells," Cancer Res. 43(7):3165-3169.

Palmer et al. (2000) "Melanocortin-1 Receptor Polymorphisms and Risk of Melanoma: Is the Association Explained Solely by Pigmentation Phenotype," Am. J. Hum. Genet. 66(1):176-186.

Sanchez et al. (2002) "Loss-of-Function Variants of the Human Melanocortin-1 Receptor Gene in Melanoma Cells Define Structural Determinants of Receptor Function," Eur. J. Biochem. 269(24):6133-6141.

Sawyer et al. (Oct. 1980) "4-Norleucine, 7-D-Phenylalanine-Aplpha-Melanocyte-Stimulating Hormone: A Highly Potent Alpha-Melanotropin with Ultralong Biological Activity," Proc. Natl. Acad. Sci. USA 77(10):5754-5758.

Schioth et al. (1999) "Loss of Function Mutations of the Human Melanocortin 1 Receptor are Common and are Associated with Red Hair." Biochem. Biophys. Res. Commun. 260(2):488-491.

Scott et al. (2002) "Human Melanocortin 1 Receptor Variants, Receptor Function and Melanocyte Response to UV Radiation," J. Cell. Sci. 115(11):2349-2355.

Smith et al. (1998) "Melanocortin 1 Receptor Variants in an Irish Population," J. Invest. Dermatol. 111(1):119-122.

Sturm et al. (Oct. 2002) "Skin Colour and Skin Cancer—MC1R, The Genetic Link," Melanoma Res. 12(5):406-416.

Sturm et al. (2003) "Genetic Association and Cellular Function of MC1R Variant Alleles in Human Pigmentation," Ann. N.Y. Acad Sci. 994:348-358.

Valverde et al. (1996) "The Asp84Glu Variant of the Melanocortin 1 Receptor (MC1R) is Associated with Melanoma," Hum. Mol. Genet. 5(10):1663-1666.

* cited by examiner

SEQUENCE LISTING

```
<160> NUMBER OF SEQ ID NOS: 6

<210> SEQ ID NO 1
<211> LENGTH: 20
<212> TYPE: DNA
<213> ORGANISM: Artificial
<220> FEATURE:
<223> OTHER INFORMATION: Synthetic construct:  oligonucleotide useful as
      a primer.

<400> SEQUENCE: 1
tggacaggac tatggctgtg                                                    20

<210> SEQ ID NO 2
<211> LENGTH: 19
<212> TYPE: DNA
<213> ORGANISM: Artificial
<220> FEATURE:
<223> OTHER INFORMATION: Synthetic construct:  oligonucleotide useful as
      a primer

<400> SEQUENCE: 2
tcttcagcac gctcttcat                                                     19

<210> SEQ ID NO 3
<211> LENGTH: 20
<212> TYPE: DNA
<213> ORGANISM: Artificial
<220> FEATURE:
<223> OTHER INFORMATION: Synthetic construct:  oligonucleotide useful as
      a primer.

<400> SEQUENCE: 3
cttctacgca ctgcgctacc                                                    20

<210> SEQ ID NO 4
<211> LENGTH: 20
<212> TYPE: DNA
<213> ORGANISM: Artificial
<220> FEATURE:
<223> OTHER INFORMATION: Synthetic construct:  oligonucleotide useful as
      a primer.

<400> SEQUENCE: 4
```

```
gctttaagtg tgctgggcag                                                 20
```

```
<210> SEQ ID NO 5
<211> LENGTH: 7
<212> TYPE: PRT
<213> ORGANISM: Artificial
<220> FEATURE:
<223> OTHER INFORMATION: Synthetic construct:  oligopeptide analog of
      MSH.
<220> FEATURE:
<221> NAME/KEY: MISC_FEATURE
<222> LOCATION: (1)..(1)
<223> OTHER INFORMATION: At position 1, Xaa is Acetyl-norleucine.
<220> FEATURE:
<221> NAME/KEY: MISC_FEATURE
<222> LOCATION: (7)..(7)
<223> OTHER INFORMATION: At position 7,  Xaa is Lysine-NH2.

<400> SEQUENCE: 5

Xaa Glu His Phe Arg Trp Xaa
1               5

<210> SEQ ID NO 6
<211> LENGTH: 7
<212> TYPE: PRT
<213> ORGANISM: Artificial
<220> FEATURE:
<223> OTHER INFORMATION: Synthetic construct:  oligopeptide analog of
      MSH.
<220> FEATURE:
<221> NAME/KEY: MISC_FEATURE
<222> LOCATION: (1)..(1)
<223> OTHER INFORMATION: At position 1, Xaa is Acetyl-norleucine.
<220> FEATURE:
<221> NAME/KEY: MISC_FEATURE
<222> LOCATION: (7)..(7)
<223> OTHER INFORMATION: At position 7,  Xaa is Lysine-NH2.

<400> SEQUENCE: 6

Xaa Asp His Phe Arg Trp Xaa
1               5
```

METHOD OF INDUCING MELANOGENESIS IN HUMANS WITH MC1R VARIANT ALLELES

CROSS-REFERENCE TO RELATED APPLICATIONS

This application is the National Stage of International Application No. PCT/AU2004/001630, filed Nov. 23, 2004, which claims priority to the Australian patent application number 2003906813, filed Nov. 24, 2003, both of which are hereby incorporated by reference to the extent not inconsistent with the disclosure hereof.

FIELD OF THE INVENTION

The present invention relates broadly to a method of inducing melanogenesis in humans, that is stimulating the production of melanins by the pigment-producing cells (keratinocytes and/or melanocytes) of the skin, in particular in humans having a loss-of-function or diminished function mutation(s) in the melanocortin-1-receptor gene.

BACKGROUND OF THE INVENTION

Non-melanoma skin cancer (NMSC) is now the most common form of cancer in white populations and incidence rates for NMSC and malignant melanoma are increasing steadily world wide. While ultraviolet radiation (UVR) is the greatest environmental risk factor for skin cancer, skin pigmentation phenotype appears to be the most important genetic determinant of risk.

The melanocortins include a family of peptide hormones that induce pigmentation by interaction with melanocortin 1 receptors (MC1R) in the epidermis (see Hadley, M E. The melanotropic hormones, In: Brake, D., editor. *Endocrinology*, 4$^{th}$ Edition, Simon & Schuster; 1982; pp. 153-76). The primary pigmentary hormone that is released from the pars intermedia of the pituitary gland in some non-human animals, and from UV-B exposed keratinocytes in human skin, is α-melanocyte stimulating hormone (α-MSH). This 13 amino acid peptide binds to MC1R to induce cyclic AMP-mediated signal transduction leading to the synthesis of melanin polymers from DOPA precursors. Two types of melanins can be expressed in humans. The brownish-black pigment eumelanin is believed to convey protection from sun damage, whereas the reddish, sulfur-containing pigment, phaeomelanin is often expressed in light-skinned human populations that report a poor tanning response to sunlight. These poorly-tanning, easily-burning populations, often possess defects in the MC1R gene [28], and are generally thought to be at a greater risk of developing both melanoma and non-melanoma skin cancers [5, 21].

α-MSH binds MC1R to stimulate both eumelanogenesis, by upregulating tyrosinase activity, and melanocyte proliferation, through activation of adenylate cyclase [1, 6, 13]. Eumelanin is known to have photoprotective properties as it is resistant to photodegradation and has the ability to quench reactive oxygen radicals [19, 20]. Studies investigating whether variant alleles affect the interaction between α-MSH, MC1R and the downstream processes have found that the MC1R gene is highly polymorphic and variants such as Arg151Cys, Arg160Trp and Asp294His, are associated with fair skin colour and red hair, characterised by a low melanin content and a low eumelanin to phaeomelanin ratio [5, 16, 28]. Several variants, including the above-mentioned, have since been associated with an increased risk of skin cancer independent of pigmentation phenotype [4, 17, 21]. It has also been demonstrated that the variants Arg142His, Arg151Cys, Arg160Trp and Asp294His are loss-of-function alleles, and one effect of having these variant alleles is a decrease in the binding affinity of MC1R to α-MSH [11, 15, 22, 24, 27]. Investigations conducted into human MC1R variants have established that either "loss-of-function" or "diminished function" mutations in the MC1R gene sensitise human melanocytes to the DNA damaging effects of UV radiation, which may increase skin cancer [12, 24, 25].

Although (α-MSH stimulates natural skin protection, the process requires harmful UVR. It has previously been disclosed that a super-potent derivative of α-MSH, Melanotan-1, (Nle$^4$-D-Phe$^7$-α-MSH), can induce tanning in human volunteers [18]. Melanotan (MT-1), contains two amino acid substitutions and exhibits a 10- to 100-fold increased activity in frog and lizard bioassays for pigmentation [25], increases melanogenesis and tyrosinase activity in human melanocytes, and more specifically, induces significant increases in the eumelanin content of melanocytes while having a lesser effect on the levels of phaeomelanin [7, 13, 14]. Several studies have assessed the pharmacokinetic and tanning effects of Melanotan in humans and found a significant increase in eumelanin, but not phaeomelanin, content in skin [7, 18]. Although melanotropins have been postulated to effect immunologic changes, all of the prior trials reported only minimal side effects such as facial flushing and transient GI upset, unless doses greater than those needed for tanning were administered.

U.S. Pat. No. 4,457,864 (issued Jul. 3, 1984), discloses analogues of α-MSH, including Nle$^4$-D-Phe$^7$-α-MSH. Cyclic analogues of α-MSH are disclosed in U.S. Pat. No. 4,485,039 (issued Nov. 27, 1984). The use of these and other analogues of α-MSH for stimulating the production of melanin by integumental melanocytes is disclosed in Australian Patent No. 597630 (dated Jan. 23, 1987) and U.S. Pat. No. 4,866,038 (issued Sep. 12, 1989), U.S. Pat. No. 4,918,055 (issued Apr. 17, 1990) and U.S. Pat. No. 5,049,547 (issued Sep. 17, 1991). Australian Patent No. 618733 (dated May 20, 1988), and U.S. Pat. No. 5,674,839 (issued Oct. 7, 1997), U.S. Pat. No. 5,683,981 (issued Nov. 4, 1997) and U.S. Pat. No. 5,714,576 (issued Feb. 3, 1998) disclose further linear and cyclic α-MSH fragment analogues, and the use of these biologically-active analogues in stimulating melanocytes. The contents of all these published Australian and US patents are incorporated herein by reference.

In work leading to the present invention, it has been demonstrated that notwithstanding the significantly reduced response to α-MSH of human melanocytes having either "loss-of-function" or "diminished function" mutations, Melanotan is effective in inducing melanogenesis in human subjects having MC1R variant alleles. In particular, it has been demonstrated that significant increases in melanin density can be induced in such subjects by use of Melanotan, in some cases leading to melanin density levels similar to the levels in subjects having the wild-type MC1R.

Accordingly, the method of the present invention enables the induction of melanogenesis in human subjects having a "loss-of-function" or "diminished function" mutation(s) in the MC1R gene, leading to increased melanin density levels in these subjects and reduced risk of skin cancer.

SUMMARY OF THE INVENTION

Bibliographic details of the publications referred to in this specification by reference number are collected at the end of the specification.

Throughout this specification, unless the context requires otherwise, the word "comprise", or variations such as "comprises" or "comprising", will be understood to imply the inclusion of a stated integer or step or group of integers or steps but not the exclusion of any other integer or step or group of integers or steps.

Those skilled in the art will appreciate that the invention described herein is susceptible to variations and modifications other than those specifically described. It is to be understood that the invention includes all such variations and modifications, the invention also includes all of the steps, features, compositions and compounds referred to or indicated in this specification, individually or collectively, and any and all combinations or any two or more of said steps or features.

In one aspect, the present invention provides a method for inducing melanogenesis in a human subject having an MC1R variant allele associated with loss of or diminished receptor function, which comprises the step of administering to said subject an amount of an α-MSH analogue effective to induce melanogenesis by the melanocytes in the skin or other epidermal tissue of the subject.

In another aspect, the present invention provides the use of an α-MSH analogue in the manufacture of a preparation for inducing melanogenesis in a human subject having an MC1R variant allele associated with loss of or diminished receptor function.

DETAILED DESCRIPTION OF THE INVENTION

Figure 1:
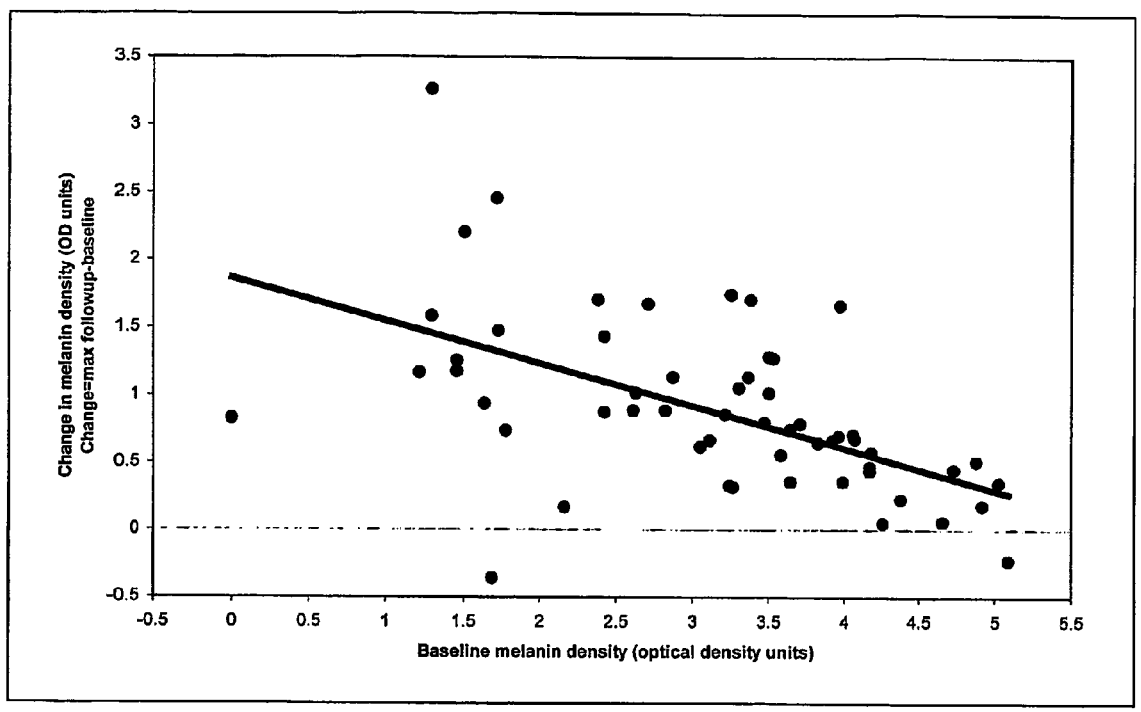
FIG. 1 shows the association between maximum change in melanin density and baseline melanin density at the inner upper arm in intent-to-treat (ITT) individuals.

α-MSH stimulation of the MC1 receptor following UV exposure is central to the tanning response in human melanocytes. One of the many effects of α-MSH is to increase the eumelanin: phaeomelanin ratio thereby increasing the photoprotective properties of the basal and suprabasal layers of the skin [2, 7]. The interaction between α-MSH and MC1R is affected by the presence of gene sequence variants in the receptor. Variation in the MC1R gene sequence is extremely common, for example, it has been shown that over 75% of the UK population harbour coding region variants [26] and in the present study 68% of a group of Australian volunteers had one or more variant alleles. Variations have been found in over 80% of individuals with red hair and/or fair skin that tan poorly but in fewer than 20% of individuals with brown or black hair and in less than 4% of those who showed a good tanning response [2, 3]. This suggests that in humans, as in other mammals, the MC1R is a key point in the regulation of pigmentation phenotype and, more importantly, that variations in this protein are associated with a poor tanning response.

As described above, the present invention provides a method for inducing melanogenesis in a human subject having an MC1R variant allele associated with loss of or diminished receptor function, which comprises the step of administering to said subject an amount of an α-MSH analogue effective to induce melanogenesis by the melanocytes in the skin or other epidermal tissue of the subject.

Human subjects having an MC1R variant allele associated with loss of or diminished receptor function, demonstrated by a reduced response to α-MSH, have a so-called "loss-of-function" or "diminished function" mutation in the MC1R gene. The melanocytes of such subjects may be either homozygous or heterozygous for such variations, and the loss of receptor function associated with the variation may vary from full to only partial loss of function. Those with a partial loss of function are referred to as "diminished function" alleles. Particular variant alleles which are relevant to the method of the present invention include, by way of example, Val60Leu (V60L), Asp84Glu (D84E), Val92Met (V92M), Arg142His (R142H), Arg151Cys (R151C), Arg160Trp (R160W), and Asp294His (D294H). The present invention extends to induction of melanogenesis in human subjects having one or more of these "loss-of-function" or "diminished function" MC1R variant alleles.

In its broadest aspects, the present invention extends to the use of an α-MSH analogue. These analogues may be synthesised according to the procedures set out in the patent documents referred to herein, or according to methods used in preparing synthetic α-MSH which are well-known to persons skilled in this art.

The term "α-MSH analogue" referred to herein is defined as a derivative of α-MSH which exhibits agonist activity for the melanocortin-1 receptor (MC1R), the receptor to which α-MSH binds to initiate the production of melanin within a melanocyte. Such derivatives include derivatives in which (i) one or more amino acid residues are deleted from the native α-MSH molecule at the N-terminal end, the C-terminal end, or both; and/or (ii) one or more amino acid residues of the native α-MSH molecule are replaced by another natural, non-natural or synthetic amino acid residue; and/or (iii) an intramolecular interaction forms as a cyclic derivative.

The use of any α-MSH analogue is contemplated in the compositions and methods described herein. Several derivatives of α-MSH have been synthesized. The α-MSH analogues described in U.S. Pat. Nos. 4,457,864, 4,485,039, 4,866,038, 4,918,055, 5,049,547, 5,674,839 and 5,714,576 and Australian Patents Nos. 597630 and 618733, which are herein incorporated by reference for their teachings with respect to α-MSH analogues and the synthesis thereof, can be used the methods described herein.

In one aspect, the α-MSH analogue may be a compound as disclosed in Australian Patent No. 597630, selected from:
(a) compounds of the formula:

Ac-Ser-Tyr-Ser-M-Gln-His-D-Phe-Arg-Trp-Gly-Lys-Pro-Val-NH$_2$ wherein M is Met, Nle or Lys; and
(b) compounds of the formula:

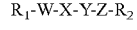
R$_1$-W-X-Y-Z-R$_2$ wherein
R$_1$ is Ac-Gly-, Ac-Met-Glu, Ac-Nle-Glu-, or Ac-Tyr-Glu-;
W is -His- or -D-His-;
X is -Phe-, -D-Phe-, -Tyr-, -D-Tyr-, or -(pNO$_2$)D-Phe$^7$-;
Y is -Arg- or -D-Arg-;
Z is -Trp- or -D-Trp-; and
R$_2$ is —NH$_2$; -Gly-NH$_2$; or -Gly-Lys-NH$_2$.

In another aspect, the α-MSH analogue may be selected from cyclic analogues which are disclosed in Australian Patent No. 618733 where an intramolecular interaction (such as a disulfide or other covalent bond) exists (1) between the amino acid residue at position 4 and an amino acid residue at position 10 or 11, and/or (2) between the amino acid residue at position 5 and the amino acid residue at position 10 or 11.

The α-MSH analogue may be a linear analogue as disclosed in U.S. Pat. No. 5,674,839, selected from the group consisting of:

Ac-Ser-Tyr-Ser-Nle-Glu-His-D-Phe-Arg-Trp-Lys-Gly-Pro-Val-NH$_2$

Ac-Ser-Tyr-Ser-Nle-Asp-His-D-Phe-Arg-Trp-Lys-Gly-Pro-Val-NH$_2$

Ac-Nle-Glu-His-D-Phe-Arg-Trp-Lys-Gly-Pro-Val-NH$_2$

Ac-Nle-Asp-His-D-Phe-Arg-Trp-Lys-Gly-Pro-Val-NH$_2$

Ac-Nle-Asp-His-D-Phe-Arg-Trp-Gly-NH$_2$

Ac-Nle-Glu-His-D-Phe-Arg-Trp-Lys-NH$_2$

Ac-Nle-Asp-His-D-Phe-Arg-Trp-Lys-NH$_2$

Ac-Nle-Glu-His-D-Phe-Arg-Trp-Orn-NH$_2$

Ac-Nle-Asp-His-D-Phe-Arg-Trp-Orn-NH$_2$

Ac-Nle-Glu-His-D-Phe-Arg-Trp-Dab-NH$_2$

Ac-Nle-Asp-His-D-Phe-Arg-Trp-Dab-NH$_2$

Ac-Nle-Glu-His-D-Phe-Arg-Trp-Dpr-NH$_2$

Ac-Nle-Glu-His-Phe-Arg-Trp-Lys-NH$_2$   (SEQ ID NO.:5)

Ac-Nle-Asp-His-Phe-Arg-Trp-Lys-NH$_2$   (SEQ ID NO.:6)

The α-MSH analogue may also be a cyclic analogue as disclosed in U.S. Pat. No. 5,674,839, selected from the group consisting of:

Ac-Nle-Glu-His-D-Phe-Arg-Trp-Lys-Gly-Pro-Val-NH$_2$ (cyclic)

Ac-Nle-Glu-His-D-Phe-Arg-Trp-Lys-NH$_2$ (cyclic)

Ac-Nle-Asp-His-D-Phe-Arg-Trp-Lys-NH$_2$ (cyclic)

Ac-Nle-Asp-His-D-Phe-Arg-Trp-Orn-NH$_2$ (cyclic)

Ac-Nle-Asp-His-D-Phe-Arg-Trp-Dab-NH$_2$ (cyclic)

Ac-Nle-Asp-His-D-Phe-Arg-Trp-Dpr-NH$_2$ (cyclic)

Ac-Ser-Tyr-Ser-Nle-Asp-His-D-Phe-Arg-Trp-Lys-Gly-Pro-Val-NH$_2$ (cyclic)

Ac-Ser-Try-Ser-Nle-Asp-His-D-Phe-Arg-Trp-Lys-NH$_2$ (cyclic)

Ac-Tyr-Ser-Nle-Asp-His-D-Phe-Arg-Trp-Lys-NH$_2$ (cyclic)

Ac-Ser-Nle-Asp-His-D-Phe-Arg-Trp-Lys-NH$_2$ (cyclic)

Ac-Nle-Asp-His-D-Phe-Arg-Trp-Lys-NH$_2$ (cyclic)

Ac-Nle-Asp-His-D-Phe-Arg-Trp-Lys-Gly-NH$_2$ (cyclic)

Ac-Nle-Asp-His-D-Phe-Arg-Trp-Lys-Gly-Pro-NH$_2$ (cyclic)

Ac-Nle-Asp-His-D-Phe-Arg-Trp-Lys-Gly-Pro-Val-NH$_2$ (cyclic)

Ac-Ser-Nle-Asp-His-D-Phe-Arg-Trp-Lys-Gly-Pro-Val-NH$_2$ (cyclic)

Where referred to herein, Ala=alanine, Arg=arginine, Dab=2,4-diaminobutyric acid, Dpr=2,3-diaminopropionic acid, Glu=glutamic acid, Gly=glycine, His=histidine, Lys=lysine, Met=methionine, Nle=norleucine, Orn=ornithine, Phe=phenylalanine, (pNO$_2$)Phe=paranitrophenylalanine, Plg=phenylglycine, Pro=proline, Ser=serine, Trp=tryptophan, TrpFor=N$^1$-formyl-tryptophan, Tyr=tyrosine, Val=valine. All peptides are written with the acyl-terminal end at the left and the amino terminal end to the right; the prefix "D" before an amino acid designates the D-isomer configuration, and unless specifically designated otherwise, all amino acids are in the L-isomer configuration.

In one aspect, the alpha-MSH analogue can be

[D-Phe$^7$]-α-MSH, [Nle$^4$, D-Phe$^7$]-α-MSH,

[D-Ser$^1$, D-Phe$^7$]-α-MSH, [D-Tyr$^2$, D-Phe$^7$]-α-MSH,

[D-Ser$^3$, D-Phe$^7$]-α-MSH, [D-Met$^4$, D-Phe$^7$]-α-MSH,

[D-Glu$^5$, D-Phe$^7$]-α-MSH, [D-His$^6$, D-Phe$^7$]-α-MSH,

[D-Phe$^7$, D-Arg$^8$]-α-MSH, [D-Phe$^7$, D-Trp$^9$]-α-MSH,

[D-Phe$^7$, D-Lys$^{11}$]-α-MSH, [D-Phe$^7$, D-Pro$^{12}$]-α-MSH,

[D-Phe$^7$, D-Val$^{13}$]-α-MSH, [D-Ser$^1$, Nle$^4$, D-Phe$^7$]-α-MSH,

[D-Tyr$^2$, Nle$^4$, D-Phe$^7$]-α-MSH, [D-Ser$^3$, Nle$^4$, D-Phe$^7$]-α-MSH,

[Nle$^4$, D-Glu$^5$, D-Phe$^7$]-α-MSH, [Nle$^4$, D-His$^6$, D-Phe$^7$]-α-MSH,

[Nle$^4$, D-Phe$^7$, D-Arg$^8$]-α-MSH, [Nle$^4$, D-Phe$^7$, D-Trp$^8$]-α-MSH,

[Nle$^4$, D-Phe$^7$, D-Lys$^{11}$]-α-MSH, [Nle$^4$, D-Phe$^7$, D-Pro$^{12}$]-α-MSH,

[Nle$^4$, D-Phe$^7$, D-Val$^{13}$]-α-MSH, [Cys$^4$, Cys$^{10}$]-α-MSH (cyclic)

[Cys$^4$, D-Phe$^7$, Cys$^{10}$]-α-MSH  [Cys$^4$, Cys$^{11}$]-α-MSH

[Cys$^5$, Cys$^{10}$]-α-MSH  [Cys$^5$, Cys$^{11}$]-α-MSH

[Cys$^4$, Cys$^{10}$]-α-MSH$_{4-13}$  [Cys$^4$, Cys$^{10}$]-α-MSH$_{4-12}$

[Nle$^4$, D-Phe$^7$]-α-MSH$_{4-10}$, [Nle$^4$, D-Phe$^7$]-α-MSH$_{4-11}$,

[D-Phe$^7$]-α-MSH$_{5-11}$, [Nle$^4$, D-Tyr$^7$]-α-MSH$_{4-11}$,

[(pNO$_2$)D-Phe$^7$]-α-MSH$_{4-11}$, [Tyr$^4$, D-Phe$^7$]-α-MSH$_{4-10}$,

[Tyr$^4$, D-Phe$^7$]-α-MSH$_{4-11}$, [Nle$^4$]-α-MSH$_{4-11}$,

[Nle$^4$, (pNO$_2$)D-Phe$^7$]-α-MSH$_{4-11}$, [Nle$^4$, D-His$^6$]-α-MSH$_{4-11}$,

[Nle$^4$, D-His$^6$, D-Phe$^7$]-α-MSH$_{4-11}$, [Nle$^4$, D-Arg$^8$]-α-MSH$_{4-11}$,

[Nle$^4$, D-Trp$^9$]-α-MSH$_{4-11}$, [Nle$^4$, D-Phe$^7$, D-Trp$^9$]-α-MSH$_{4-11}$,

[Nle$^4$, D-Phe$^7$]-α-MSH$_{4-9}$, or [Nle$^4$, D-Phe$^7$, D-Trp$^9$]-α-MSH$_{4-9}$.

In a further aspect, the α-MSH analogue is

[Nle$^4$,D-Phe$^7$]-α-MSH$_{4-10}$,

[Nle$^4$,D-Phe$^7$]-α-MSH$_{4-11}$,

[Nle$^4$,D-Phe$^7$,D-Trp$^9$]-α-MSH$_{4-11}$, or

[Nle$^4$,D-Phe$^7$]-α-MSH$_{4-9}$.

The most preferred α-MSH analogue for use in the methods of this invention is [Nle$^4$,D-Phe$^7$]-α-MSH, referred to hereinafter as "Melanotan-1" or "MT-1".

The present invention also extends to the use of an α-MSH analogue in the manufacture of a preparation for inducing melanogenesis in a human subject having an MC1R variant allele associated with loss of or diminished receptor function.

The α-MSH analogues used of this invention may be administered by a variety of routes including oral, parenteral or transdermal. The term "parenteral" is used herein to encompass any method by which the compounds according to the present invention are introduced into the systemic circulation and include intravenous, intramuscular and subcutaneous injections. The term "transdermal" as used herein encompasses the administration of the compound by topical methods such as buccal or skin patches, intranasal or tracheal sprays, by solution for use as ocular drops, by suppositories for vaginal or anal routes of administration or by conventional topical preparations such as creams or gels for localised percutaneous delivery.

The compounds will be formulated in suitable compositions determined by the intended means of administration, according to methods and procedures well-known to those skilled in the art (see, for example, *Remington's Pharmaceutical Sciences*, 18$^{th}$ Edition, Mack Publishing Company, Pennsylvania, USA). For example, the compounds suitable for use in this invention may be formulated or compounded into pharmaceutical compositions comprising at least one compound of the present invention (the compositions may comprise one compound or admixtures of compounds according to the present invention) in admixture with a solid or liquid pharmaceutical excipient such as a diluent or carrier for oral or parenteral administration. As injection medium, water containing the usual pharmaceutical additives for injection solutions, such as stabilising agents, solubilising agents, and buffers is preferred. Among additives of this type are, for example, tartrate and citrate buffers, ethanol, complex forming agents such as ethylenediamine-tetraacetic acid, and high molecular weight polymers such as liquid polyethylene oxide for viscosity regulation. Solid carrier materials include, for example, starch, lactose, mannitol, methyl cellulose, talc, highly dispersed silicic acid, high molecular weight fatty acids such as stearic acid, gelatine, agar-agar, calcium phosphate, magnesium stearate, animal and vegetable fats, and high molecular weight polymers such as polyethylene glycols. Compositions suitable for oral administration can, if desired, contain flavouring and/or sweetening agents. For topical administration, the compounds may be preferably used with various conventional bases for topical preparations such as creams, ointments, gels, lotions or sprays, depending upon the desired mode of delivery of the ingredients to an individual. In manufacturing these preparations, the composition may also be mixed with conventional inert excipients such as thickening agents, emollients, surfactants, pigments, perfumes, preservatives, fillers and emulsifiers, all of which are well known and conventionally used in the formulation of transdermal or other preparations. Typically, these non-active ingredients will make up the greater part of the final preparation. Preferably, the compositions are manufactured to allow for controlled and/or sustained-release delivery.

The actual amount of administered compound according to the present invention may vary between fairly wide ranges depending upon the mode of administration, the excipients used, and the degree of stimulation desired. Such amounts are well within the skill of the pharmaceutical scientist to determine, and the amount administered to the mammal may be any amount chosen to stimulate melanotropic activity, for example, by formulation as an implant using poly (D,L lactide-co-glycolide polymer or a similar biodegradable, biocompatible polymer as carrier.

It will be appreciated that the actual preferred amounts of the α-MSH analogue in a specified case will vary according to the specific compounds being utilized, the particular compositions formulated, the mode of application, and the particular situs and subject being treated. Dosages for a given host can be determined using conventional considerations, e.g., by customary comparison of the differential activities of the subject compounds and of a known agent, e.g., by means of an appropriate conventional pharmacological protocol. Physicians and formulators, skilled in the art of determining doses of pharmaceutical compounds, will have no problems determining doses for inducing melanogenesis by the methods described herein.

The present invention is further described by reference to the following non-limiting Example.

EXAMPLE

1. Introduction

There is compelling evidence that melanotropic peptides may provide a potential for increasing melanin pigmentation of human skin. Synthetic MSH may be used to enhance skin pigmentation of normal or light-skinned individuals to protect them from the hazards of solar radiation. Several studies have suggested that individuals whose skin tends to burn easily on exposure to the sun and does not tan readily are at higher risk of both nonmelanoma skin tumours and of cutaneous melanoma. There is unambiguous evidence that UV radiation is responsible for skin cancer in humans. In the face of increased deterioration of the ozone layer, especially in Australia, and the increasing incidence of and mortality from skin cancer, the ability to stimulate the skin's own "protective mechanism" of tanning may prove extremely important as photoprotective strategy.

In Melanotan, the substitution of amino acids at positions 4 and 7 of α-MSH makes this analogue 10-1000 times more active than α-MSH in one or more bioassays [23]. The pharmacological action of Melanotan is quite prolonged as evidenced by sustained maximal tyrosinase stimulation in cultured mouse melanoma cells. The prolonged activity may result partially from its resistance to degradation by serum enzymes or proteolytic enzymes.

Intraperitoneal delivery of Melanotan to foetal rats and mice to had no teratogenic or toxicological effects. In addition, standard toxicology tests on mice, rats, guinea pigs and miniature pigs using subcutaneous and intraperitoneal injection routes have shown no significant toxicities. Several studies on human volunteers have been performed under a Physician's IND in the U.S. These studies, in over 100 subjects, have clearly demonstrated that Melanotan can induce safe and effective tanning in humans over a dose range of 0.08 to 0.4 mg/Kg/day for 10 days [7, 18] with follow-up to 12 months. Pharmacokinetic data has indicated that Melanotan has a half-life after subcutaneous administration of about 30 minutes with little or no activity in the plasma after 6 hours.

2. Materials and Methods

2.1. Subjects and Treatment

Seventy-seven Caucasian individuals were recruited into a double-blind, randomised, placebo-controlled study from study centres in Adelaide and Sydney, Australia as part of a large phase II study to determine the photoprotective effect of Melanotan in a Caucasian population. The study involved 57 treated and 20 placebo subjects, and was conducted in accordance with the currently accepted Declaration of Helsinki and ICH guidelines for Good Clinical Practice (GCP) including written informed consent from all subjects. Individuals were selected from a Caucasian population covering a Fitzpatrick skin type range of I to IV where: type I—always burn, never tan; type II—usually burn, tan less than average; type III—sometimes mild burn, tan about average; and type IV—rarely burn, tan more than average [10]. Subjects were randomly assigned on a 3:1 active:placebo basis to receive three 10 day series of subcutaneous injections of either 0.16 mg/kg/day of Melanotan or 0.01 mL/kg/day of sterile saline. Each series of injections was administered at a clinic beginning at days 1, 29 and 57 of the study with weekends omitted. Patients were advised to use SPF 25+ sunscreen when outside for longer than 30 minutes, but to otherwise not modify their usual sun exposure patterns.

2.2. Outcome Measures

Skin pigmentation was measured at the upper inner arm using a non-invasive quantitative skin chromaticity (reflectance) reading at 400 nm and 420 nm in order to determine melanin content. Melanin density (MD) is obtained using the formula described by Dwyer et al, 1998 [8] where: MD=100× (0.035307+0.009974(R420–R400)). An MD unit represents epidermal melanin density as routinely determined by optical density measurement of light microscopy sections stained for melanin granules. For Caucasians, this generally ranges from 1 to 5 density units [9]. Readings of reflectance were taken before treatment at Visit 2 and at Visit 12 (Day 12), Visit 14 (Day 30), Visit 22 (Day 40), Visit 26 (Day 60) and Visit 34 (Day 90). One subject had a negative estimate of melanin density at baseline, and this was reset to zero.

2.3. DNA Extraction and MC1R Analysis

Subjects had 10 mL of blood taken for DNA extraction and MC1R analysis at the first screening visit. Genomic DNA was isolated from peripheral blood leukocytes using the Nucleon Bacc3 DNA extraction kit (Amersham International). The MC1R gene fragment was amplified in two overlapping fragments using a PC960C thermal cycler (Corbett Research, Sydney). Seven variants, previously associated with skin colour or increased skin cancer risk, were used in analysis with the melanin density measures. The primer sequences were: 5'-tggacaggactatggctgtg-3' (MC1R-1F—SEQ ID NO: 1), 5'-tcttcagcacgctcttcat-3' (MC1R-1R—SEQ ID NO: 2), 5'-cttctacgcactgcgctacc-3' (MC1R-2F—SEQ ID NO: 3) and 5'-gcttaagtgtgctgggcag-3' (MC1R-2R—SEQ ID NO: 4). For individual amplifications 20-50 ng genomic DNA template was combined with 10 mM Tris-HCl, pH8.3, 50 mM KCl, 2.0 mM MgCl2, 1 µM each of the four dNTPs, 0.8 µM of each primer, and 2.5 U Taq polymerase (Qiagen) in a 30 µl reaction. Samples were denatured for 2 min at 94° C., and amplified using 30 cycles consisting of 30 s at 94° C., 30 s at 62° C., and 30 min at 72° C., followed by a final elongation step for 10 min at 72° C. Individual PCR reactions were purified using an UltraClean PCR Clean-up Kit (MO BIO Laboratories, Inc.). Forward and reverse sequences were amplified as recommended using an Applied Biosystem Big Dye Terminator Cycle Sequencing Kit (Applied Biosystem). Sequencing reactions were ethanol precipitated as described in the ABI User Manual. Pellets were resuspended in 15 µl Template Suppression Reagent, denatured at 95° C. for 2 min and then loaded onto an ABI Prism 310 Genetic Analyser (Applied Biosystem). Both forward and reverse sequences of both MC1R fragments were sequenced and analysed using Sequencher 4.1 software (Gene Codes Corporation).

2.4. Statistical Methods

The primary analysis was based on the intent-to-treat (ITT) principle, with the last observation carried forward for subjects with missing data. All subjects randomised to receive study treatment were included in the ITT population.

Linear regression models were built to examine the relationship between treatment group and outcome of interest with adjustment for confounders (also called analysis of covariance (ANCOVA)). The basic set of confounders for multivariable analysis included month of initial consultation, baseline melanin density, recruitment site and age. The outcomes examined were change in melanin density (final measurement minus baseline measurement) and maximum change in melanin density (largest follow-up measurement minus baseline measurement).

To determine whether Melanotan increased the melanin density to a greater extent in individuals carrying variant alleles than in wildtype individuals, regression was again used but the analysis now restricted to those subjects assigned to the treatment group. Each of the seven regression models, corresponding to the seven different alleles, included a term for the presence or absence of the allele as well as baseline melanin density. The significance of the effect of the allele was based on the p-value associated with the t-test for the allele term in the model. Modelling for the effect of the red hair variants proceeded in a similar fashion. When examining the effect of the number of variants on the increase in melanin density, the number of variants was fitted as a linear term in the regression model to assess dose-response effects. Although the inclusion of month of initial consultation in these models consistently diluted the effect of the alleles, it was decided to present results unadjusted for month because the biological mechanism was not clear. Results of statistical tests were regarded as statistically significant if the associated p-values were less than 0.05. No adjustment has been made for multiple testing. All treatment findings, both positive and negative, are reported.

3. Results

3.1. Melanotan and Melanin Density

Seventy-seven subjects were treated with a series of three 10 day subcutaneous injections of either 0.16 mg/kg/day of Melanotan or 0.01 mL/kg/day of sterile saline. Subjects treated with Melanotan had a mean (standard error) increase in melanin density of 0.73 (0.09) units, and subjects receiving saline treatment had a mean decrease in melanin density of 0.30 (0.10) units. There was a significant ($p<0.001$) increase in melanin density in the treated group compared to the placebo group with an unadjusted mean (standard error) difference of 1.04 (0.16) (Table 1).

To assess the change in pigmentation in the treatment group overall, a plot was generated of the maximum change in melanin density compared with the equivalent baseline value for each subject. The result is shown in FIG. 1 and demonstrates that the lower the starting melanin density, the greater the effect of drug treatment.

3.2. MC1R Genotype and Melanotan

The entire coding region of the MC1R gene of each individual was sequenced and the genotype of seven variants, which have been suggested to increase risk of skin cancer, was determined (Table 2). The majority of subjects were assessed as skin type I/II category and it was found that 68% carried at least one of the variants investigated, which is similar to the frequency found in other studies when looking at the number of variants present in skin type I populations [4, 17]. The mean baseline melanin density was lower in the presence of a variant allele in all cases except in the placebo carriers of the Val60Leu or Asp294His allele. The presence of a red hair variant (Arg151Cys, Arg160Trp or Asp294His) was also reflected by a lower mean baseline melanin density.

Changes in melanin density for subjects in the treatment group, cross-classified by presence of variants, are shown in Table 3. Subjects with a Val60Leu allele had a mean increase in melanin density of 1.07 units, compared with 0.57 for subjects without the allele. This difference was statistically significant ($p=0.03$) after adjustment for differences in baseline melanin density (data not shown). In general, the variant carriers had a greater change in melanin density than non-carriers, except for those with an Asp294His allele. Subjects were also grouped by the number of variants of any type, and by the presence (or absence) of the red hair variant (Table 4). The mean increase in melanin density for wild type subjects was 0.36 units (10%), compared to 0.83 units (27%) and 1.09 units (40%) for one and two variant carriers respectively. This dose response effect remained statistically significant after adjustment for differences in baseline melanin density ($p=0.01$). There were no statistical differences in the increase in melanin density according to presence of the red hair variants.

4. Discussion

The current study is the first to investigate the effect of Melanotan in humans with a variant MC1R genotype. The data presented here demonstrates that Melanotan causes a greater increase in melanin density in variant carriers than in wildtype subjects (Table 4). This result is particularly interesting because it demonstrates that individuals with a variant MC1R genotype, and therefore at increased risk for skin cancer, can benefit from a drug previously suspected to only work in wildtype MC1R individuals. Furthermore, Dwyer et al. recently concluded from measurements of cutaneous melanin density at the upper inner arm of Caucasian men living in Australia, that those with 0-1 melanin units were associated with approximately 7 times greater relative risk of malignant melanoma or basal cell carcinoma than men with >3 melanin units [9]. If the Melanotan-induced increase in melanin density at the upper inner arm affected risk in a similar way, the 1-2 unit increase observed in this study could conceivably provide significant additional protection against sun-induced skin cancer.

TABLE 1

Mean (Standard Error) measurement of baseline and final Melanin Density (optical density units) in treated and placebo individuals at the upper inner arm.

| | Treatment MD | Placebo MD | Difference between Treatment and Placebo Mean ± SE | |
|---|---|---|---|---|
| | Mean ± SE | Mean ± SE | Unadjusted | Adjusted* |
| Baseline | 3.16 ± 0.15 | 3.43 ± 0.22 | | |
| Final | 3.89 ± 0.13 | 3.13 ± 0.17 | | |
| Change (final-baseline) | 0.73 ± 0.09 (+23%) | −0.30 ± 0.10 (−9%) | 1.04 ± 0.16 $p < 0.001$ | 0.96 ± 0.14 $p < 0.001$ |

*Adjusted for baseline melanin density

TABLE 2

Mean (standard error) baseline melanin density of treated and placebo individuals, by MC1R variant.

| | Treatment N = 57 | | Placebo N = 20 | |
|---|---|---|---|---|
| Variant Status | n (%) | Mean ± SE | n (%) | Mean ± SE |
| | | Val60Leu | | |
| G/G | 38 (67) | 3.34 ± 0.17 | 11 (55) | 3.33 ± 0.26 |
| G/T | 17 (30) | 2.89 ± 0.32 | 9 (45) | 3.56 ± 0.38 |
| T/T | 2 (3) | 2.06 ± 0.55 | 0 (0) | n.a. |
| | | Asp84Glu | | |
| C/C | 55 (97) | 3.17 ± 0.16 | 20 (100) | 3.43 ± 0.22 |
| C/A | 2 (3) | 2.96 ± 0.09 | 0 (0) | n.a. |
| | | Val92met | | |
| G/G | 46 (81) | 3.19 ± 0.18 | 19 (95) | 3.40 ± 0.23 |
| G/A | 11 (19) | 3.01 ± 0.25 | 1 (5) | 4.09 |
| | | Arg142His | | |
| G/G | 56 (98) | 3.19 ± 0.15 | 19 (95) | 3.48 ± 0.22 |
| G/T | 1 (2) | 1.46 | 0 (0) | n.a. |
| G/A | 0 (0) | n.a. | 1 (5) | 2.53 |
| | | Arg151Cys | | |
| C/C | 47 (82) | 3.19 ± 0.17 | 16 (80) | 3.53 ± 0.26 |
| C/T | 10 (18) | 3.03 ± 0.40 | 4 (20) | 3.05 ± 0.35 |
| | | Arg160Trp | | |
| C/C | 51 (89) | 3.18 ± 0.17 | 20 (100) | 3.43 ± 0.22 |
| C/T | 6 (11) | 3.01 ± 0.32 | 0 (0) | n.a. |
| | | Asp294His | | |
| G/G | 56 (98) | 3.18 ± 0.15 | 17 (85) | 3.40 ± 0.24 |
| G/C | 1 (2) | 2.16 | 3 (15) | 3.60 ± 0.54 |
| | | MC1R gene: | | |
| No variants (Wild type) | 20 (35) | 3.62 ± 0.25 | 5 (25) | 3.57 ± 0.45 |
| One variant | 22 (39) | 3.04 ± 0.25 | 12 (60) | 3.34 ± 0.30 |
| Two variants | 15 (26) | 2.71 ± 0.26 | 3 (15) | 3.60 ± 0.54 |
| | | Red hair carrier | | |
| No | 41 (72) | 3.21 ± 0.19 | 13 (65) | 3.51 ± 0.30 |
| Yes | 16 (28) | 3.02 ± 0.27 | 7 (35) | 3.29 ± 0.30 |

TABLE 3

Results of Melanin density changes (inner upper arm) by variant status in 57 individuals allocated to treatment group

| Variant Allele | No. of subjects | No. of alleles | Baseline MD Mean ± SE | MD Change Mean ± SE |
|---|---|---|---|---|
| Val60Leu | 19 | 21 | 2.80 ± 0.29 | 1.07 ± 0.17 |
| Asp84Glu | 2 | 2 | 2.96 ± 0.09 | 0.88 ± 0.26 |
| Val92Met | 11 | 11 | 3.01 ± 0.25 | 1.03 ± 0.12 |
| Arg142His | 1 | 1 | 1.46 | 1.18 |
| Arg151Cys | 10 | 10 | 3.03 ± 0.40 | 0.85 ± 0.33 |
| Arg160Trp | 6 | 6 | 3.01 ± 0.32 | 0.94 ± 0.31 |
| Asp294His | 1 | 1 | 2.16 | −0.23 |

TABLE 4

Results of Melanin density changes (inner upper arm) by variant status in 57 individuals allocated to treatment group.

| Variant Allele | No. of subjects | Baseline MD Mean ± SE | MD Change Mean ± SE (% change) | p-value* |
|---|---|---|---|---|
| MC1R gene: | | | | |
| No variants (Wild type) | 20 | 3.62 ± 0.25 | 0.36 ± 0.09 (10) | Reference |
| One variant | 22 | 3.04 ± 0.25 | 0.83 ± 0.13 (27) | 0.06 |
| Two variants | 15 | 2.71 ± 0.26 | 1.09 ± 0.21 (40) | 0.01 |
| Red hair carrier | | | | |
| No | 41 | 3.21 ± 0.19 | 0.68 ± 0.09 (21) | Reference |
| Yes | 16 | 3.02 ± 0.27 | 0.88 ± 0.23 (29) | 0.40 |

*p-value associated with test of whether mean change in melanin density amongst the variant group is greater than amongst those in the reference group after adjustment for baseline melanin density.

REFERENCES

[1] Abdel-Malek Z, Swope V B, Suzuki I, Akcali C, Harriger M D, Boyce S T, Urabe K, Hearing V J. Mitogenic and melanogenic stimulation of normal human melanocytes by melanotropic peptides. *Proc Natl Acad Sci USA* (1995); 92 (5); 1789-1793.

[2] Abdel-Malek Z, Suzuki I, Tada A, Im S, Akcali C. The melanocortin-1 receptor and human pigmentation. *Ann NY Acad Sci* (1999); 885; 117-133.

[3] Abdel-Malek Z, Scott M C, Suzuki I, Tada A, Im S, Lamoreux L, Ito S, Barsh G, Hearing V J. The melanocortin-1 receptor is a key regulator of human cutaneous pigmentation. *Pigment Cell Res* (2000); 13 Suppl 8; 156-162.

[4] Bastiaens M T, ter Huume J A, Kielich C, Gruis N A, Westendorp R G, Vermeer B J, Bavinck J N. Melanocortin-1 receptor gene variants determine the risk of nonmelanoma skin cancer independently of fair skin and red hair. *Am J Hum Genet* (2001); 68 (4); 884-894.

[5] Box N F, Wyeth J R, O'Gorman L E, Martin N G, Sturm R A. Characterization of melanocyte stimulating hormone receptor variant alleles in twins with red hair. *Hum Mol Genet* (1997); 6 (11); 1891-1897.

[6] De Luca M, Siegrist W, Bondanza S, Mathor M, Cancedda R, Eberle A N. Alpha melanocyte stimulating hormone (alpha MSH) stimulates normal human melanocyte growth by binding to high-affinity receptors. *J Cell Sci* (1993); 105 (Pt 4); 1079-1084.

[7] Dorr R T, Dvorakova K, Brooks C, Lines R, Levine N, Schram K, Miketova P, Hruby V, Alberts D S. Increased eumelanin expression and tanning is induced by a superpotent melanotropin [Nle4-D-Phe7]-alpha-MSH in humans. *Photochem Photobiol.* (2000); 72 (4); 526-532.

[8] Dwyer T, Muller H K, Blizzard L, Ashbolt R, Phillips G. The use of spectrophotometry to estimate melanin density in Caucasians. *Cancer Epidemiol Biomarkers Prev* (1998); 7 (3); 203-206.

[9] Dwyer T, Blizzard L, Ashbolt R, Plumb J, Berwick M, Stankovich J M. Cutaneous melanin density of Caucasians measured by spectrophotometry and risk of malignant melanoma, basal cell carcinoma, and squamous cell carcinoma of the skin. *Am J Epidemiol* (2002); 155 (7); 614-621.

[10] Fitzpatrick T B. The validity and practicality of sun-reactive skin types I through VI. *Arch Dermatol* (1988); 124 (6); 869-871.

[11] Frandberg P A, Doufexis M, Kapas S, Chhajlani V. Human pigmentation phenotype: a point mutation generates nonfunctional MSH receptor. *Biochem Biophys Res Commun* (1998); 245 (2); 490-492.

[12] Healy E, Jordan S A, Budd P, Suffolk R, Rees J. Jackson I. Functional variation of MC1R alleles from red-haired individuals. *Hum Mol Genet* (2001); 10 (21): 2397-2402

[13] Hunt G, Todd C, Cresswell J E, Thody A J. Alpha-melanocyte stimulating hormone and its analogue Nle4DPhe7 alpha-MSH affect morphology, tyrosinase activity and melanogenesis in cultured human melanocytes. *J Cell Sci* (1994); 107 (Pt 1); 205-211.

[14] Hunt G, Kyne S, Wakamatsu K, Ito S, Thody A J. Nle4DPhe7 alpha-melanocyte-stimulating hormone increases the eumelanin:phaeomelanin ratio in cultured human melanocytes. *J Invest Dermatol* (1995); 104 (1); 83-85.

[15] Jimenez-Cervantes C, Germer S, Gonzalez P, Sanchez J, Sanchez C O, Garcia-Borron J C. Thr40 and Met122 are new partial loss-of-function natural mutations of the human melanocortin 1 receptor. *FEBS Lett* (2001); 508 (1); 44-48.

[16] John P R, Ramsay M. Four novel variants in MC1R in red-haired South African individuals of European descent: S83P, Y152X, A171D, P256S. *Hum Mutat* (2002); 19 (4); 461-462.

[17] Kennedy C, ter Huume J, Berkhout M, Gruis N, Bastiaens M, Bergman W, Willemze R, Bavinck J N. Melanocortin 1 receptor (MC1R) gene variants are associated with an increased risk for cutaneous melanoma which is largely independent of skin type and hair color. *J Invest Dermatol* (2001); 117 (2); 294-300.

[18] Levine N, Shettel S N, Eytan T, Dorr R T, Hadley M E, Weinrach J C, Ertl G A, Toth K, McGee D L, Hruby V J. Induction of skin tanning by subcutaneous administration of a potent synthetic melanotropin. *Jama* (1991); 266 (19); 2730-2736.

[19] Menon I A, Persad S, Haberman H F, Kurian C J. A comparative study of the physical and chemical properties of melanins isolated from human black and red hair. *J Invest Dermatol* (1983); 80 (3); 202-206.

[20] Menon I A, Persad S, Ranadive N S, Haberman H F. Effects of ultraviolet-visible irradiation in the presence of melanin isolated from human black or red hair upon Ehrlich ascites carcinoma cells. *Cancer Res* (1983); 43 (7); 3165-3169.

[21] Palmer J S, Duffy D L, Box N F, Aitken J F, O'Gorman L E, Green A C, Hayward N K, Martin N G, Sturm R A. Melanocortin-1 receptor polymorphisms and risk of melanoma: is the association explained solely by pigmentation phenotype? *Am J Hum Genet* (2000); 66 (1); 176-186.

[22] Sanchez Mas J, Olivares Sanchez C, Ghanem G, Haycock J, Lozano Teruel J A, Garcia-Borron J C, Jimenez-Cervantes C. Loss-of-function variants of the human melanocortin-1 receptor gene in melanoma cells define structural determinants of receptor function. *Eur J Biochem* (2002); 269 (24); 6133-6141.

[23] Sawyer T K, Sanfilippo P J, Hruby V J, Engel M H, Heward C B, Burnett J B, Hadley M E. 4-Norleucine, 7-D-phenylalanine-alpha-melanocyte-stimulating hormone: a highly potent alpha-melanotropin with ultralong biological activity. *Proc Natl Acad Sci USA* (1980); 77 (10); 5754-5758.

[24] Schioth H B, Phillips S R, Rudzish R, Birch-Machin M A, Wikberg J E, Rees J L. Loss of function mutations of the human melanocortin 1 receptor are common and are associated with red hair. *Biochem Biophys Res Commun* (1999); 260 (2); 488-491.

[25] Scott M C, Wakamatsu K, Ito S, Kadekaro A L, Kobayashi N, Groden J, Kavanagh R, Takakuwa T, Virador V, Hearing V J, Abdel-Malek Z A, Human melanocortin 1 receptor variants, receptor function and melanocyte response to UV radiation. *J Cell Sci* (2002); 115 (Pt 11); 2349-2355.

[26] Smith R, Healy E, Siddiqui S, Flanagan N. Steijlen P M, Rosdahl I, Jacques J P, Rogers S, Turner R, Jackson I J, Birch-Machin M A, Rees J L. Melanocortin 1 receptor variants in an Irish population. *J Invest Dermatol* (1998); 11 (1); 119-122.

[27] Sturm R A, Duffy D L, Box N F, Newton R A, Shepherd A G, Chen W, Marks L H, Leonard J H, Martin N G. Genetic association and cellular function of MC1R variant alleles in human pigmentation. *Ann NY Acad Sci* (2003); 994; 348-358.

[28] Valverde P, Healy E, Sikkink S, Haldane F, Thody A J, Carothers A, Jackson I J, Rees J L. The Asp84Glu variant of the melanocortin 1 receptor (MC1R) is associated with melanoma. *Hum Mol Genet* (1996); 5 (10); 1663-1666.

The invention claimed is:

1. A method for inducing melanogenesis in a human subject having a melanocortin 1 receptor (MC1R) variant allele associated with loss of or diminished receptor function, which comprises the steps of:
   i) identifying the MC1R variant using primer sequences selected from 5'-tggacaggactatggctgtg-3' (MC1R-1F—SEQ ID NO:1), 5'-tcttcagcacgctcttcat-3' (MC1R-1R—SEQ ID NO:2), 5'cttctacgcactgcgctacc-3' (MC1R-2F—SEQ ID NO: 3) and 5'-gctttaagtgtgctgggcag-3' (MC1R-2R—SEQ ID NO: 4), and
   ii) administering to said subject an amount of [Nle$^4$, DPhe$^7$]-α-melanocyte stimulating hormone ([Nle$^4$, DPhe$^7$]-α-MSH) effective to induce melanogenesis by the melanocytes in the skin or other epidermal tissue of the subject.

2. The method of claim 1, wherein an admixture of said [Nle$^4$, DPhe$^7$]-α-MSH with a further α-MSH analogue is administered in an amount effective to induce said melanogenesis, wherein said further α-MSH analogue is selected from:
   (a) compounds of the formula:

Ac-Ser-Tyr-Ser-M-Gln-His-D-Phe-Arg-Trp-Gly-Lys-Pro-Val-NH$_2$ wherein M is Met, Nle or Lys; and
   (b) compounds of the formula:

R$_1$—W—X—Y—Z—R$_2$ wherein
   R$_1$ is Ac-Gly-, Ac-Met-Glu, Ac-Nle-Glu-, or Ac-Tyr-Glu-;
   W is -His- or -D-His-;
   X is -Phe-, -D-Phe-, -Tyr-, -D-Tyr-, or -(pNO$_2$)D-Phe$^7$-;
   Y is -Arg- or -D-Arg-;
   Z is -Trp- or -D-Trp-; and
   R$_2$ is -NH$_2$; -Gly-NH$_2$; or -Gly-Lys-NH$_2$.

3. The method of claim 1, wherein an admixture of said [Nle$^4$, DPhe$^7$]-α-MSH with a further α-MSH analogue is administered in an amount effective to induce said melanogenesis, wherein the further α-MSH analogue is selected from the group consisting of:

Ac-Ser-Tyr-Ser-Nle-Glu-His-D-Phe-Arg-Trp-Lys-Gly-Pro-Val-NH$_2$,

Ac-Ser-Tyr-Ser-Nle-Asp-His-D-Phe-Arg-Trp-Lys-Gly-Pro-Val-NH$_2$,

Ac-Nle-Glu-His-D-Phe-Arg-Trp-Lys-Gly-Pro-Val-NH$_2$,

Ac-Nle-Asp-His-D-Phe-Arg-Trp-Lys-Gly-Pro-Val-NH$_2$,

Ac-Nle-Asp-His-D-Phe-Arg-Trp-Gly-NH₂,

Ac-Nle-Glu-His-D-Phe-Arg-Trp-Lys-NH₂,

Ac-Nle-Asp-His-D-Phe-Arg-Trp-Lys-NH₂,

Ac-Nle-Glu-His-D-Phe-Arg-Trp-Orn-NH₂,

Ac-Nle-Asp-His-D-Phe-Arg-Trp-Orn-NH₂,

Ac-Nle-Glu-His-D-Phe-Arg-Trp-Dab-NH₂,

Ac-Nle-Asp-His-D-Phe-Arg-Trp-Dab-NH₂,

Ac-Nle-Glu-His-D-Phe-Arg-Trp-Dpr-NH₂,

Ac-Nle-Glu-His-Phe-Arg-Trp-Lys-NH₂ (SEQ ID NO:5)

, and

Ac-Nle-Asp-His-Phe-Arg-Trp-Lys-NH₂ (SEQ ID NO:6)

.

4. The method of claim 1, wherein an admixture of said [Nle⁴, DPhe⁷]-α-MSH with a further α-MSH analogue is administered in an amount effective to induce said melanogenesis wherein the further α-MSH analogue is selected from the group consisting of:

Ac-Nle-Glu-His-D-Phe-Arg-Trp-Lys-Gly-Pro-Val-NH₂,

Ac-Nle-Glu-His-D-Phe-Arg-Trp-Lys-NH₂,

Ac-Nle-Asp-His-D-Phe-Arg-Trp-Lys-NH₂,

Ac-Nle-Asp-His-D-Phe-Arg-Trp-Orn-NH₂,

Ac-Nle-Asp-His-D-Phe-Arg-Trp-Dab-NH₂,

Ac-Nle-Asp-His-D-Phe-Arg-Trp-Dpr-NH₂,

Ac-Ser-Tyr-Ser-Nle-Asp-His-D-Phe-Arg-Trp-Lys-Gly-Pro-Val-NH₂,

Ac-Ser-Try-Ser-Nle-Asp-His-D-Phe-Arg-Trp-Lys-NH₂,

Ac-Tyr-Ser-Nle-Asp-His-D-Phe-Arg-Trp-Lys-NH₂,

Ac-Ser-Nle-Asp-His-D-Phe-Arg-Trp-Lys-NH₂,

Ac-Nle-Asp-His-D-Phe-Arg-Trp-Lys-NH₂,

Ac-Nle-Asp-His-D-Phe-Arg-Trp-Lys-Gly-NH₂,

Ac-Nle-Asp-His-D-Phe-Arg-Trp-Lys-Gly-Pro-NH₂,

Ac-Nle-Asp-His-D-Phe-Arg-Trp-Lys-Gly-Pro-Val-NH₂, and

Ac-Ser-Nle-Asp-His-D-Phe-Arg-Trp-Lys-Gly-Pro-Val-NH₂.

5. The method of claim 1, wherein an admixture of said [Nle⁴, DPhe⁷]-α-MSH with a further α-MSH analogue is administered in an amount effective to induce said melanogenesis wherein the further α-MSH analogue is:

[D-Phe⁷]-α-MSH, [Nle⁴, D-Phe⁷]-α-MSH,

[D-Ser¹, D-Phe⁷]-α-MSH, [D-Tyr², D-Phe⁷]-α-MSH,

[D-Ser³, D-Phe⁷]-α-MSH, [D-Met⁴, D-Phe⁷]-α-MSH,

[D-Glu⁵, D-Phe⁷]-α-MSH, [D-His⁶, D-Phe⁷]-α-MSH,

[D-Phe⁷, D-Arg⁸]-α-MSH, [D-Phe⁷, D-Trp⁹]-α-MSH,

[D-Phe⁷, D-Lys¹¹]-α-MSH, [D-Phe⁷, D-Pro¹²]-α-MSH,

[D-Phe⁷, D-Val¹³]-α-MSH, [D-Ser¹, Nle⁴, D-Phe⁷]-α-MSH,

[D-Tyr², Nle⁴, D-Phe⁷]-α-MSH, [D-Ser³, Nle⁴, D-Phe⁷]-α-MSH,

[Nle⁴, D-Glu⁵, D-Phe⁷]-α-MSH, [Nle⁴, D-His⁶, D-Phe⁷]-α-MSH,

[Nle⁴, D-Phe⁷, D-Arg⁸]-α-MSH, [Nle⁴, D-Phe⁷, D-Trp⁸]-α-MSH,

[Nle⁴, D-Phe⁷, D-Lys¹¹]-α-MSH, [Nle⁴, D-Phe⁷, D-Pro¹²]-α-MSH,

[Nle⁴, D-Phe⁷, D-Val¹³]-α-MSH, [Cys⁴, Cys¹⁰]-α-MSH,

[Cys⁴, D-Phe⁷, Cys¹⁰]-α-MSH, [Cys⁴, Cys¹¹]-α-MSH,

[Cys⁵, Cys¹⁰]-α-MSH, [Cys⁵, Cys¹¹]-α-MSH,

[Cys⁴, Cys¹⁰]-α-MSH₄₋₁₃, [Cys⁴, Cys¹⁰]-α-MSH₄₋₁₂,

[Nle⁴, D-Phe⁷]-α-MSH₄₋₁₀, [Nle⁴, D-Phe⁷]-α-MSH₄₋₁₁,

[D-Phe⁷]-α-MSH₅₋₁₁, [Nle⁴, D-Tyr⁷]-α-MSH₄₋₁₁,

[(pNO₂)D-Phe⁷]-α-MSH₄₋₁₁, [Tyr⁴, D-Phe⁷]-α-MSH₄₋₁₀,

[Tyr⁴, D-Phe⁷]-α-MSH₄₋₁₁, [Nle⁴]-α-MSH₄₋₁₁,

[Nle⁴, (pNO₂)D-Phe⁷]-α-MSH₄₋₁₁, [Nle⁴, D-His⁶]-α-MSH₄₋₁₁,

[Nle⁴, D-His⁶, D-Phe⁷]-α-MSH₄₋₁₁, [Nle⁴, D-Arg⁸]-α-MSH₄₋₁₁,

[Nle⁴, D-Trp⁹]-α-MSH₄₋₁₁, [Nle⁴, D-Phe⁷, D-Trp⁹]-α-MSH₄₋₁₁,

[Nle⁴, D-Phe⁷]-α-MSH₄₋₉, or [Nle⁴, D-Phe⁷, D-Trp⁹]-α-MSH₄₋₉.

6. The method of claim 1, wherein an admixture of said [Nle⁴, DPhe⁷]-α-MSH with a further α-MSH analogue is administered in an amount effective to induce said melanogenesis wherein the further α-MSH analogue is:

[Nle⁴,D-Phe⁷]-α-MSH₄₋₁₀,

[Nle⁴,D-Phe⁷]-α-MSH₄₋₁₁,

[Nle⁴,D-Phe⁷]-α-MSH₄₋₁₁, or

[Nle⁴,D-Phe⁷]-α-MSH₄₋₉.

7. A method according to claim 1 wherein the human subject has one or more variant alleles selected from the group consisting of Val60Leu (V60L), Asp84Glu (D84E), Val92Met (V92M), Arg142His (R142H), Arg 151Cys (R151C), Arg160Trp (R160W), and Asp294His (D294H).

8. A method according to claim 1 wherein the human subject has two or more variant alleles selected from the group consisting of Val60Leu (V60L), Asp84Glu (D84E), Val92Met (V92M), Arg142His (R142H), Arg 151Cys (R151C), Arg160Trp (R160W), and Asp294His (D294H).

9. A method according to claim 1 wherein the human subject has a Fitzpatrick skin type of I or II.

* * * * *